(12) United States Patent
Lord et al.

(10) Patent No.: US 9,135,810 B2
(45) Date of Patent: Sep. 15, 2015

(54) METHOD, APPARATUS AND SYSTEM FOR ASSIGNING REMOTE CONTROL DEVICE TO AMBULATORY MEDICAL DEVICE

(75) Inventors: Peter Carl Lord, Kihei, HI (US); Brian Michael Shelton, Northridge, CA (US); Scott R. Gibson, Granada Hills, CA (US); Daniel Hernandez Villegas, Grenada Hills, CA (US); Jon Douglas Newbill, Simi Valley, CA (US); Joseph Wayne Vandegriff, Lago Vista, TX (US)

(73) Assignee: MEDALLION THERAPEUTICS, INC., Santa Clara, CA (US)

( * ) Notice: Subject to any disclaimer, the term of this patent is extended or adjusted under 35 U.S.C. 154(b) by 1946 days.

(21) Appl. No.: 11/932,856

(22) Filed: Oct. 31, 2007

(65) Prior Publication Data
US 2008/0132973 A1 Jun. 5, 2008

Related U.S. Application Data

(60) Provisional application No. 60/867,580, filed on Nov. 28, 2006.

(51) Int. Cl.
*A61N 1/372* (2006.01)
*G08C 17/02* (2006.01)
*A61B 17/00* (2006.01)

(52) U.S. Cl.
CPC ............ *G08C 17/02* (2013.01); *A61N 1/37247* (2013.01); *A61B 2017/00017* (2013.01); *A61B 2017/00367* (2013.01); *A61B 2017/00973* (2013.01); *G08C 2201/20* (2013.01)

(58) Field of Classification Search
CPC ............ A61N 1/37522; A61N 1/3728; A61N 1/37247; G08C 17/02; A61B 2017/00367; A61B 2017/00973; A61B 2017/00017
USPC .................................................... 607/59, 60
See application file for complete search history.

(56) References Cited

U.S. PATENT DOCUMENTS

| 4,855,746 | A | 8/1989 | Stacy |
| 5,069,668 | A | 12/1991 | Boydman |
| 5,232,448 | A | 8/1993 | Zdeb |
| 5,338,157 | A | 8/1994 | Blomquist |
| 6,077,055 | A | 6/2000 | Vilks |
| 6,106,576 | A | 8/2000 | Fromson |
| 6,269,340 | B1 | 7/2001 | Ford et al. |
| 6,381,496 | B1 | 4/2002 | Meadows |

(Continued)

FOREIGN PATENT DOCUMENTS

| EP | 1 585 080 A2 | 10/2005 |
| WO | WO 03/026726 A1 | 4/2003 |
| WO | WO 2004/028596 A1 | 4/2004 |

OTHER PUBLICATIONS

U.S. Appl. No. 11/836,709: Final Rejection, Apr. 26, 2012.

*Primary Examiner* — Eric D. Bertram
(74) *Attorney, Agent, or Firm* — Henricks, Slavin & Holmes LLP

(57) ABSTRACT

A method for assigning a remote control to an ambulatory medical device includes generating and transmitting user inputs from a remote control to an ambulatory medical device, and receiving and processing the user inputs to determine whether the user inputs represent a sequence authorizing an assignment of the remote control to the ambulatory medical device.

20 Claims, 9 Drawing Sheets

(56) References Cited

U.S. PATENT DOCUMENTS

| | | |
|---|---|---|
| 6,427,088 B1 | 7/2002 | Bowman, IV et al. |
| 6,562,001 B2 | 5/2003 | Lebel et al. |
| 6,571,128 B2 | 5/2003 | Lebel et al. |
| 6,687,547 B2 | 2/2004 | Goedeke et al. |
| 6,694,334 B2 | 2/2004 | DuLong et al. |
| 6,768,425 B2 | 7/2004 | Flaherty et al. |
| 6,796,956 B2 | 9/2004 | Hartlaub et al. |
| 6,880,564 B2 | 4/2005 | Erickson |
| 6,957,655 B2 | 10/2005 | Erickson et al. |
| 7,043,305 B2 | 5/2006 | KenKnight et al. |
| 7,054,782 B2 | 5/2006 | Hartlaub |
| 7,060,031 B2 | 6/2006 | Webb et al. |
| 7,072,725 B2 | 7/2006 | Bristol et al. |
| 7,471,994 B2 | 12/2008 | Ford et al. |
| 7,551,078 B2 | 6/2009 | Carlson et al. |
| 7,945,452 B2 | 5/2011 | Fathallah et al. |
| 2001/0049673 A1 | 12/2001 | Dulong et al. |
| 2001/0056358 A1 | 12/2001 | Dulong et al. |
| 2002/0058906 A1 | 5/2002 | Lebel et al. |
| 2002/0126036 A1 | 9/2002 | Flaherty et al. |
| 2002/0138155 A1 | 9/2002 | Bristol |
| 2002/0143580 A1 | 10/2002 | Bristol et al. |
| 2002/0193679 A1 | 12/2002 | Malave et al. |
| 2003/0163088 A1 | 8/2003 | Blomquist |
| 2003/0163789 A1 | 8/2003 | Blomquist |
| 2003/0181852 A1 | 9/2003 | Mann et al. |
| 2004/0049245 A1* | 3/2004 | Gass et al. .................. 607/60 |
| 2004/0158193 A1 | 8/2004 | Bui et al. |
| 2004/0172301 A1 | 9/2004 | Mihai et al. |
| 2004/0193090 A1 | 9/2004 | Lebel et al. |
| 2004/0249477 A1 | 12/2004 | Blanpain |
| 2005/0012594 A1 | 1/2005 | Shim |
| 2005/0143864 A1 | 6/2005 | Blomquist |
| 2005/0154537 A1 | 7/2005 | Kutzko et al. |
| 2005/0177096 A1 | 8/2005 | Bollish et al. |
| 2005/0251228 A1* | 11/2005 | Hamel .......................... 607/60 |
| 2006/0100907 A1 | 5/2006 | Holland et al. |
| 2006/0129433 A1 | 6/2006 | Koneru |
| 2006/0149416 A1 | 7/2006 | Mohapatra et al. |
| 2006/0173444 A1 | 8/2006 | Choy et al. |
| 2006/0229551 A1 | 10/2006 | Martinez et al. |
| 2006/0229557 A1 | 10/2006 | Fathallah et al. |
| 2006/0235472 A1 | 10/2006 | Goetz et al. |
| 2006/0244627 A1 | 11/2006 | Kagermeier et al. |
| 2006/0265140 A1 | 11/2006 | Hartlaub |
| 2007/0118405 A1 | 5/2007 | Campbell et al. |
| 2008/0033402 A1 | 2/2008 | Blomquist |
| 2009/0043290 A1 | 2/2009 | Villegas et al. |
| 2009/0043291 A1 | 2/2009 | Thompson |
| 2009/0143580 A1 | 6/2009 | McArthur et al. |

* cited by examiner

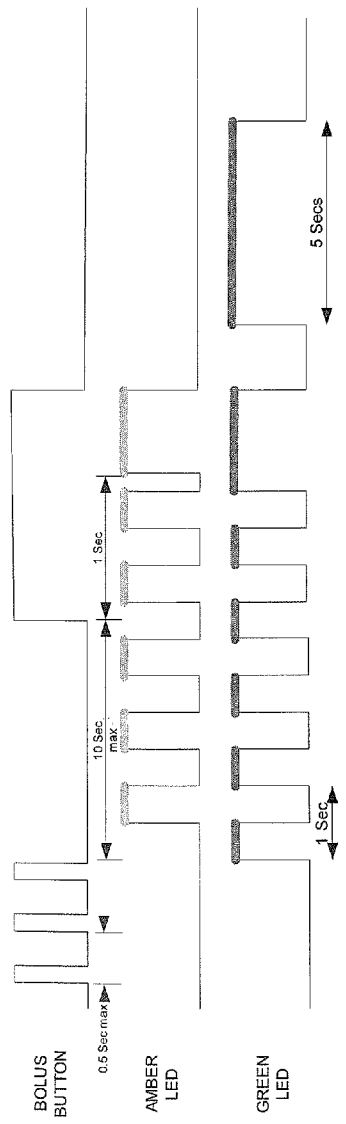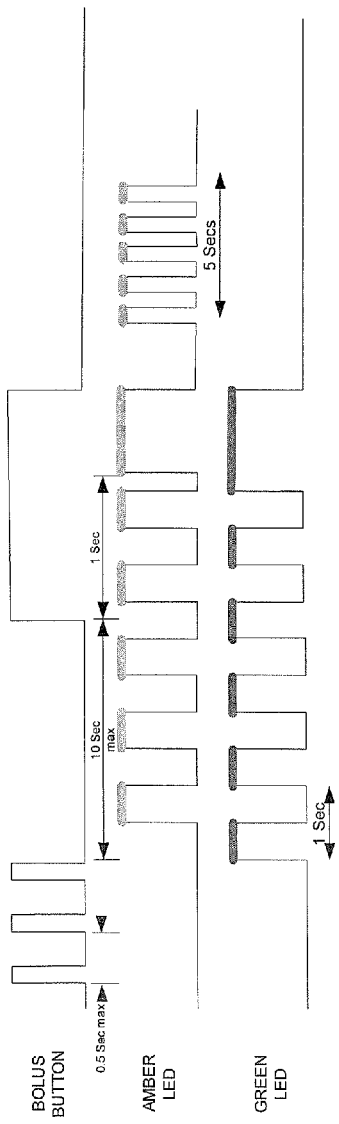

Display Lights Legend

| | |
|---|---|
| Operation in Progress <br> ▬  ▬  ▬  ▬ | Green |
| Operation Successful <br> ▬▬▬▬▬▬▬▬ | Green |
| Operation in Progress with Low Battery <br> ▪▪▪▪  ▪▪▪▪  ▪▪▪▪  ▪▪▪▪ | Green |
| Failure to Communicate with Pump <br> ▬ ▬ ▬ ▬ ▬ ▬ ▬ ▬ | Amber |
| Ready to Assign <br> ▬▬▬▬▬▬▬▬ | Amber <br> Green |
| Request Denied by Pump <br> ▪ ▪     ▪ ▪     ▪ ▪ | Amber |

FIG. 10

METHOD, APPARATUS AND SYSTEM FOR ASSIGNING REMOTE CONTROL DEVICE TO AMBULATORY MEDICAL DEVICE

CROSS-REFERENCE TO RELATED APPLICATIONS

This application claims the benefit of U.S. Provisional Application No. 60/867,580, filed on Nov. 28, 2006, which application is incorporated herein by reference.

BACKGROUND OF THE INVENTIONS

1. Field of Inventions

The present inventions relate generally to remote controls and ambulatory medical systems including remote controls.

2. Description of the Related Art

Many medical systems include a therapeutic device and a remote control with a plurality of buttons that allows a physician, technician or patient to provide an instruction to the therapeutic device by way of a telemetric signal. A remote control may, for example, be provided in combination with an ambulatory medical device such as an implantable infusion device or an implantable stimulation device. Implantable infusion devices frequently include a housing, a medication reservoir, a catheter with a discharge end, a pump or other fluid transfer device that moves the medication from the reservoir to the discharge end of the catheter, a telemetric communication device and a therapeutic device. Implantable stimulation devices may include a housing, electrodes, a source of stimulation energy, a telemetric communication device and a therapeutic device. In either case, the controller may be configured to provide basal delivery of medication or stimulation energy in accordance with instructions provided by the physician. The controller may also be configured to provide bolus delivery in response to an instruction from the patient. Such a "bolus" instruction, which can be communicated to the implantable device by way of a remote control, may come in response to a high glucose level measurement in the case of a diabetic patient, an increase in pain level in the case of a pain management patient, or some other symptom that is associated with the particular medical condition that the therapeutic device is intended to treat.

The present inventors have determined that one issue associated with the use of remote controls in medical systems, especially remote controls carried by patients, is associating (or "marrying") a specific remote control with a specific ambulatory medical device for the purpose of permitting bolus or other commands to be sent by the remote control device to the ambulatory medical device. More specifically, the present inventors have determined that known remote control devices for ambulatory medical devices are often overly complex with respect to both the user interface that they provide (e.g., too many buttons) and the procedures that they require in order to marry a new remote control device to an ambulatory medical device (e.g., when a remote is lost or misplaced).

SUMMARY OF THE INVENTIONS

In an example embodiment, a method for communicating between a remote control and an ambulatory medical device, the remote control having only a single user operated control, which single operated control is a user input mechanism adapted to be actuated by a user of the remote control to generate a user input, the remote control being adapted to facilitate a communication link with the ambulatory medical device, includes actuating the single user input mechanism of the remote control to generate a sequence of user inputs recognizable by the remote control as an instruction to generate and transmit to the ambulatory medical device via the communication link a marrying command that assigns the remote control to the ambulatory medical device enabling the ambulatory medical device to respond only to operational commands provided by the remote control.

In an example embodiment, a method for communicating between a remote control and an ambulatory medical device, the remote control including first and second user operated controls, the first user operated control is a single user input mechanism adapted to be actuated by a user of the remote control to generate a user input, the remote control being adapted to facilitate a communication link with the ambulatory medical device, the method includes, by actuating only the single user input mechanism of the remote control, generating a sequence of user inputs recognizable as an instruction to generate and transmit to the ambulatory medical device via the communication link a marrying command that assigns the remote control to the ambulatory medical device enabling the ambulatory medical device to respond only to the operational commands of the remote control.

In an example embodiment, a method of communicating between a remote control device and an ambulatory device includes marrying a remote control device with an ambulatory device by providing a predetermined sequence of user inputs using a user input mechanism on the remote control device, and after the marrying step is completed, allowing the delivery of a predetermined dosage of therapeutic treatment with the ambulatory device by activating the same user input mechanism to generate a signal to the ambulatory device to commence delivering the predetermined dosage of therapeutic treatment.

In an example embodiment, a method of operating a remote control device and ambulatory device includes generating a predetermined sequence to marry a remote control device with an ambulatory device by providing a predetermined sequence of user inputs using a user input mechanism on the remote control device, and generating a second predetermined sequence to provide a diagnostic signal to the ambulatory device using the same user input mechanism.

In an example embodiment, a method for assigning a remote control to an ambulatory medical device includes generating and transmitting user inputs from a remote control to an ambulatory medical device, and receiving and processing the user inputs to determine whether the user inputs represent a sequence authorizing an assignment of the remote control to the ambulatory medical device.

In an example embodiment, a medical device system includes a remote, the remote having only a single user operated control, which is a single user input mechanism, an ambulatory medical device, and a communication link between the remote and ambulatory medical device.

In an example embodiment, a medical device system includes a remote control including first and second user operated controls, the first user operated control being a single user input mechanism adapted to be actuated by a user of the remote control to generate user inputs, an ambulatory medical device, and a communication link between the remote and ambulatory medical device, the communication link being adapted to transmit a sequence of the user inputs generated using only the single user input mechanism to assign the remote control to the ambulatory medical device.

In an example embodiment, a remote control for use with an ambulatory medical device includes a user input mechanism adapted to be actuated to generate user inputs, a communication device adapted to facilitate a communication link between the remote control and the ambulatory medical device, and a controller adapted to control the communication device in response to the user input mechanism being actuated, and to receive and process the user inputs to determine whether the user inputs represent a sequence authorizing an assignment of the remote control to the ambulatory medical device.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of exemplary embodiments will be made with reference to the accompanying drawings.

FIGS. 9A and 9B are timing diagrams showing LED illumination for the "Assign Success" and "Assign Failure" states, respectively, of FIG. 8.

FIG. 10 is a display lights legend for a remote control device in accordance with one embodiment of the present invention.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions.

The present remote controls have application in a wide variety of medical device systems. One example of such a system is an implantable infusion device system and the present inventions are discussed in the context of implantable infusion device systems. The present inventions are not, however, limited to implantable infusion device systems and are instead also applicable to other medical device systems that currently exist, or are yet to be developed. For example, the present inventions are applicable to other ambulatory medical device systems. Such systems include, but are not limited to, externally carried infusion pump systems, implantable pacemaker and/or defibrillator systems, implantable neural stimulator systems, and implantable and/or externally carried physiologic sensor systems.

Figure 1:
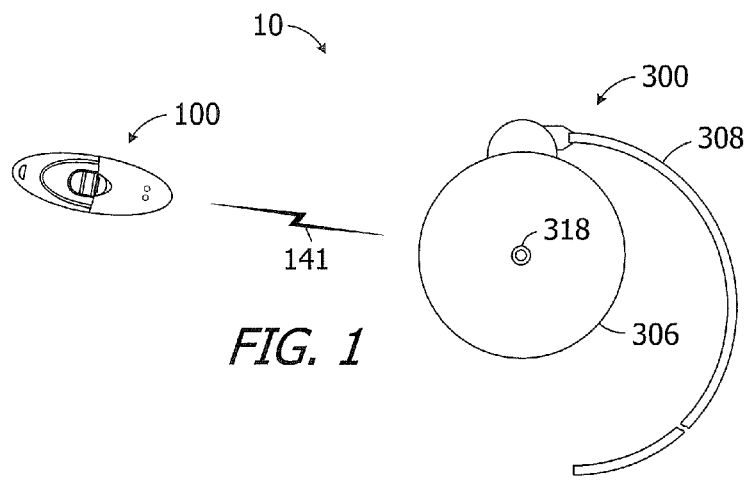
FIG. 1 is a plan view of an ambulatory medical device system in accordance with one embodiment of a present invention.
Figure 2:
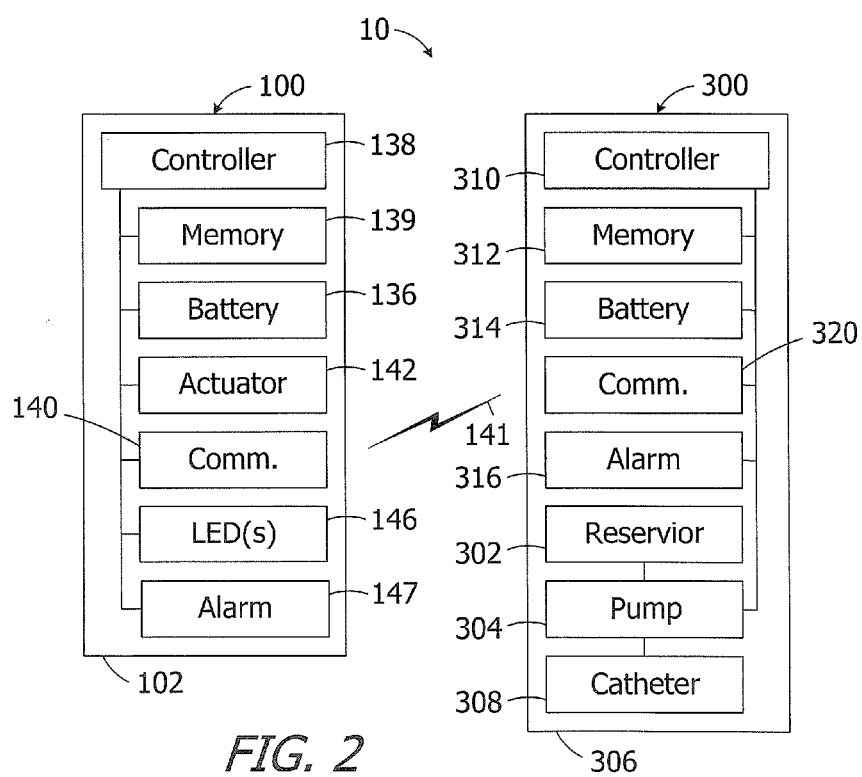
FIG. 2 is a block diagram of the ambulatory medical device system illustrated in FIG. 1.

One example of an ambulatory medical device system in accordance with the present inventions is an implantable infusion device system. The implantable infusion device system may include any one of the remote controls described herein in combination with an implantable infusion device. Referring to FIGS. 1 and 2, in an example embodiment, an implantable infusion device system 10 includes a remote control 100 and an implantable infusion device 300.

In an example embodiment, the remote control 100 includes a battery or other power source 136, a controller 138, such as a microprocessor, microcontroller or other control circuitry, memory 139, an actuator 142 with a movable element, and one or more LEDs 146 (and/or alarm 147). The memory 139 can also be contained within the controller 138 (e.g., within a microcontroller). By way of example and not of limitation, the alarm 147 can include one or more of an audio speaker and a vibration device. A communication device 140 (including an antenna if necessary) is also provided. The communication device 140 establishes a communications link 141, e.g., a radio frequency (RF) communications link, with the implantable infusion device 300. Although the present inventions are not limited to any particular communication device, in an example embodiment, the communication device 140 is a telemetry device that transmits an RF signal at a specified frequency or set of frequencies. In an example implementation, there are five channels. The RF signal may, in some instances, be a carrier signal that carriers bit streams. The communication device 140 is also configured to receive signals from the implantable infusion device 300. Other exemplary communication devices include oscillating magnetic field communication devices, static magnetic field communication devices, optical communication devices, ultrasound communication devices and direct electrical communication devices.

In this example embodiment, the implantable infusion device 300 includes a medication reservoir 302 and a pump or other fluid transfer device 304 within a housing 306. The pump 304 transfers medication from the reservoir 302 through a catheter 308 to the target region within the body. Operation of the implantable infusion device 300 is controlled by a controller 310, such as a microprocessor, microcontroller or other control circuitry, in accordance with instructions stored in memory 312. Power is provided by a battery or other power source 314. An alarm 316 (e.g., an audible alarm such as an audio speaker, and/or a vibration device) may also be provided in order to inform the patient, for example, when the amount of medication in the reservoir 302 is low or when the amount of energy stored in the battery 314 is low. A refill port 318, which allows the reservoir to be refilled while the implantable infusion device 300 is within the patient, is positioned on the exterior of the housing 306.

A communication device 320 is also provided. In this example embodiment, the communication device 320 is configured to receive signals from, and transmit signals to, the remote control 100. In an example embodiment, the communication device 320 is a telemetry device that transmits and receives RF signals at a specified frequency or set of frequencies. The RF (or other) signal may, in some instances, be a carrier signal that carriers bit streams.

Figures 3A, 3B, 3C:
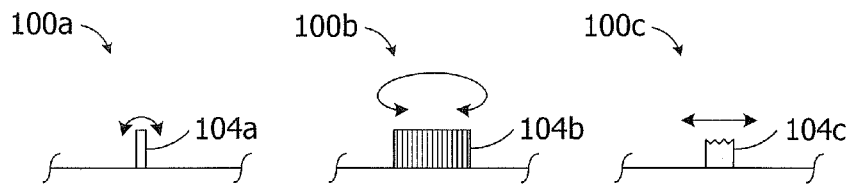
FIGS. 3A-3C illustrate alternate user input mechanisms for the remote control of FIG. 1 in the form of a positionable lever, a turnable knob, and a switch, respectively.

The remote control 100 can include one or more user input mechanisms, as well as different types of user input mechanisms. As further discussed with reference to FIGS. 11-23, in an example embodiment, the remote control 100 includes a single user operated control (e.g., button 104) which is a user input mechanism adapted to be actuated by a user of the remote control 100 to generate a user input. The single user operated control is not limited to pressable buttons. By way of example, and referring to FIGS. 3A-3C, alternate embodiments, remote control 100a, 100b, and 100c, are instead provided with a positionable lever 104a, a turnable knob 104b, and a switch 104c, respectively.

Thus, in an example embodiment, a method for communicating between a remote control and an ambulatory medical device includes actuating the single user input mechanism of the remote control to generate a sequence of user inputs recognizable by the remote control as an instruction to generate and transmit to the ambulatory medical device via the communication link a marrying command that assigns the remote control to the ambulatory medical device enabling the ambulatory medical device to respond only to operational commands provided by the remote control. In an example embodiment, the method further includes using a status indicator (e.g., one or more of the LED(s) 146, the alarm 147, and the alarm 316) to indicate the status of the remote control or the ambulatory device.

Figure 4:
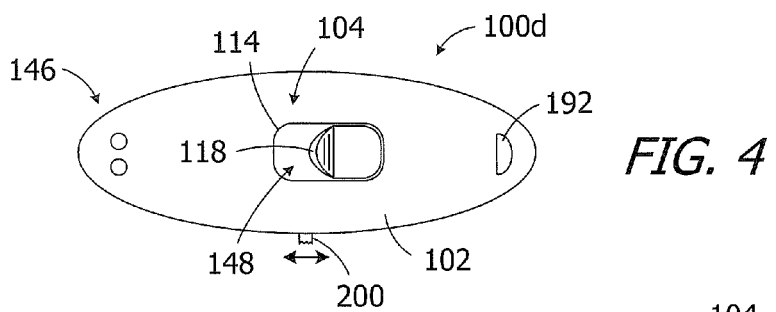
FIG. 4 illustrates an embodiment of a remote control that includes first and second user operated controls.

Referring to FIG. 4, in another example embodiment, remote control 100d includes first and second user operated controls. The first user operated control (e.g., button 104) is a single user input mechanism adapted to be actuated by a user of the remote control 100d to generate a user input; the second user operated control (e.g., ON/OFF, power or enable switch 200) is not a user input mechanism. The scope of the present invention includes remote controls with a single (i.e., only one) user input mechanism, regardless of the number of user operated controls.

Thus, in an example embodiment, a method for communicating between a remote control and an ambulatory medical device includes generating by actuating only the single user input mechanism of the remote control a sequence of user inputs recognizable as an instruction to generate and transmit to the ambulatory medical device via the communication link a marrying command that assigns the remote control to the ambulatory medical device enabling the ambulatory medical device to respond only to the operational commands of the remote control. In an example embodiment, the method further includes signaling to the user through user prompts generated by a status indicator when the sequence of user inputs has been received. In an example embodiment, the method further includes actuating the second user operated control of the remote control to enable the remote control to communicate with the ambulatory device via the communication link.

Figure 5:
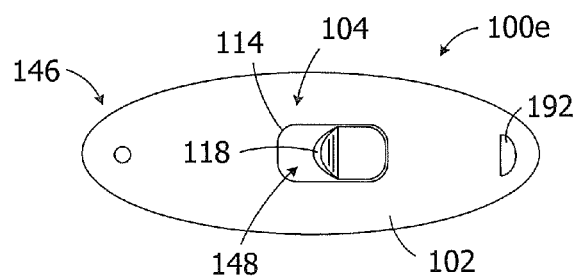
FIG. 5 illustrates an alternate embodiment of a remote control that includes only a single LED.
Figure 6:
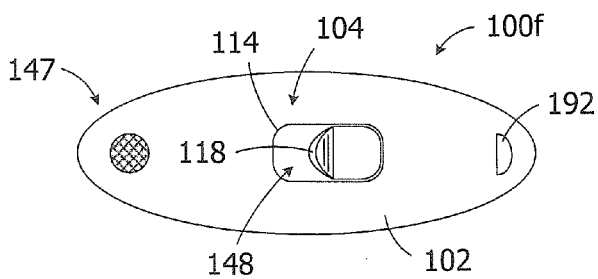
FIG. 6 illustrates an alternate embodiment of a remote control that includes an audio speaker.

Referring to FIG. 5, in another example embodiment, remote control 100e includes only a single LED 146. Referring to FIG. 6, in another example embodiment, remote control 100e includes alarm 147, instead of LED(s) 146.

During the "marrying" process, both the remote control device and the ambulatory medical device store in their respective memories the unique identifying address, number, etc. of the other device. Example "marrying" processes described herein utilize a single user input mechanism of the remote control in a manner distinguishable from other operations such a commanding a bolus or sending a diagnostic signal (pertaining to a diagnostic event). This prevents the inadvertent assigning/reassigning of a new remote control device to an ambulatory medical device.

By way of example, a diagnostic event can be a breakthough-pain episode experienced by the patient. In this case, for example, the patient pushes the button on the remote control when he or she is experiencing higher-than-normal pain. When the patient visits the clinic, the physician can review the resulting log and use it to adjust the drug delivery program (i.e., background rate). A diagnostic event can be an episode of patient overmedication. In this case, for example, the patient pushes the button on the remote control when he or she is feeling the effects of overmedication, such as lethargia. This information can also be used by the physician to adjust the drug delivery program. The remote control can be used to generate diagnostic signals to track any unintended side effect or patient activity.

In an example embodiment, a remote control for use with an ambulatory medical device includes a user input mechanism adapted to be actuated to generate user inputs, a communication device adapted to facilitate a communication link between the remote control and the ambulatory medical device, and a controller adapted to control the communication device in response to the user input mechanism being actuated, and to receive and process the user inputs to determine whether the user inputs represent a sequence authorizing an assignment of the remote control to the ambulatory medical device. In an example embodiment, the remote control has only a single user operated control, which user operated control is the user input mechanism. In an example embodiment, the single user operated control is selected from the group consisting of a pressable button, a switch, a knob, and a lever. In an example embodiment, the remote control has at least one other user operated control, in addition to the user input mechanism, wherein the at least one other user operated control is not configured to provide a sequence for marrying the remote control to the ambulatory medical device. In an example embodiment, the remote control further includes a status indicator. In an example embodiment, the controller is adapted to generate and control the communications device to transmit a command to the ambulatory medical device to generate an audible sound. In an example embodiment, the command is generated and transmitted after the sequence has been provided. In an example embodiment, the remote control further includes one or more light sources; and the controller is adapted to control the one or more light sources (e.g., two light sources). In an example embodiment, the controller is adapted to control the one or more light sources to provide a user prompt for an additional user input. In an example embodiment, the remote control further includes an audio speaker; and the controller is adapted to control the audio speaker. In an example embodiment, the controller is adapted to control the audio speaker to provide a user prompt for an additional user input. In an example embodiment, the remote control further includes a vibration device; and the controller is adapted to control the vibration device. In an example embodiment, the controller is adapted to control the vibration device to provide a user prompt for an additional user input. In an example embodiment, the remote control further includes a memory device; and the controller is adapted to store in the memory device ambulatory medical device identification information transmitted from the ambulatory medical device to the remote control via the communication link. In an example embodiment, the controller is adapted to store the ambulatory medical device identification information in the memory device after an assignment confirmation input has been provided via the user input mechanism. In an example embodiment, the controller is adapted to control the communications device to transmit remote control identification information after an assignment confirmation input has been provided via the user input mechanism.

In an example embodiment, a medical device system includes a remote, the remote having only a single user operated control, which is a single user input mechanism, an ambulatory medical device, and a communication link between the remote and ambulatory medical device. In an example embodiment, the single user operated control is adapted to be actuated by a user of the remote to generate user inputs; and the remote includes a controller adapted to control the communication link in response to the single user operated control being actuated, and to receive and process the user inputs to determine whether the user inputs represent a sequence authorizing an assignment of the remote to the ambulatory medical device.

In an example embodiment, a medical device system includes a remote control including first and second user operated controls, the first user operated control being a single user input mechanism adapted to be actuated by a user of the remote control to generate user inputs, an ambulatory medical device, and a communication link between the remote and ambulatory medical device, the communication link being adapted to transmit a sequence of the user inputs generated using only the single user input mechanism to assign the remote control to the ambulatory medical device. In an example embodiment, the remote control includes a controller adapted to control the communication link in response to the first user operated control being actuated, and to receive and process the user inputs to determine whether the user inputs represent a sequence authorizing an assignment of the remote control to the ambulatory medical device.

Once "married" to the implantable infusion device 300, the remote control 100 may be used, for example, to send a "bolus delivery" request or diagnostic signal to the implantable infusion device 300 by way of the communication devices 140 and 320 when a user input mechanism of the remote control 100 is actuated.

Referring again to FIGS. 1 and 2, in this example embodiment, the remote control controller 138 may actuate one or more of the LEDs 146 in order to confirm to the patient that the "bolus delivery" request has been transmitted. The implantable infusion device controller 310 may respond to the receipt of the "bolus delivery" request in a variety of ways. For example, the controller 310 may accept the request, actuate the fluid transfer device 304, and transmit an "acceptance" signal to the remote control 100. In response to the "acceptance" signal, the remote control controller 138 may actuate one or more of the LEDs 146 so as to indicate that that the "bolus delivery" request has been accepted.

The controller 310 may, alternatively, deny the "bolus delivery" request because the fluid transfer device 304 is already in the process of transferring medication to the catheter 308, the patient has already reached the maximum permissible number of bolus deliveries for a particular time period, or there has not been sufficient time since the last delivery of medication. A "denial" signal may also be transmitted from the infusion device 300 to the remote control 100 and, in response, the remote control controller 138 may actuate one or more of the LEDs 146 so as to indicate that the "bolus delivery" request has been denied.

Figure 7:
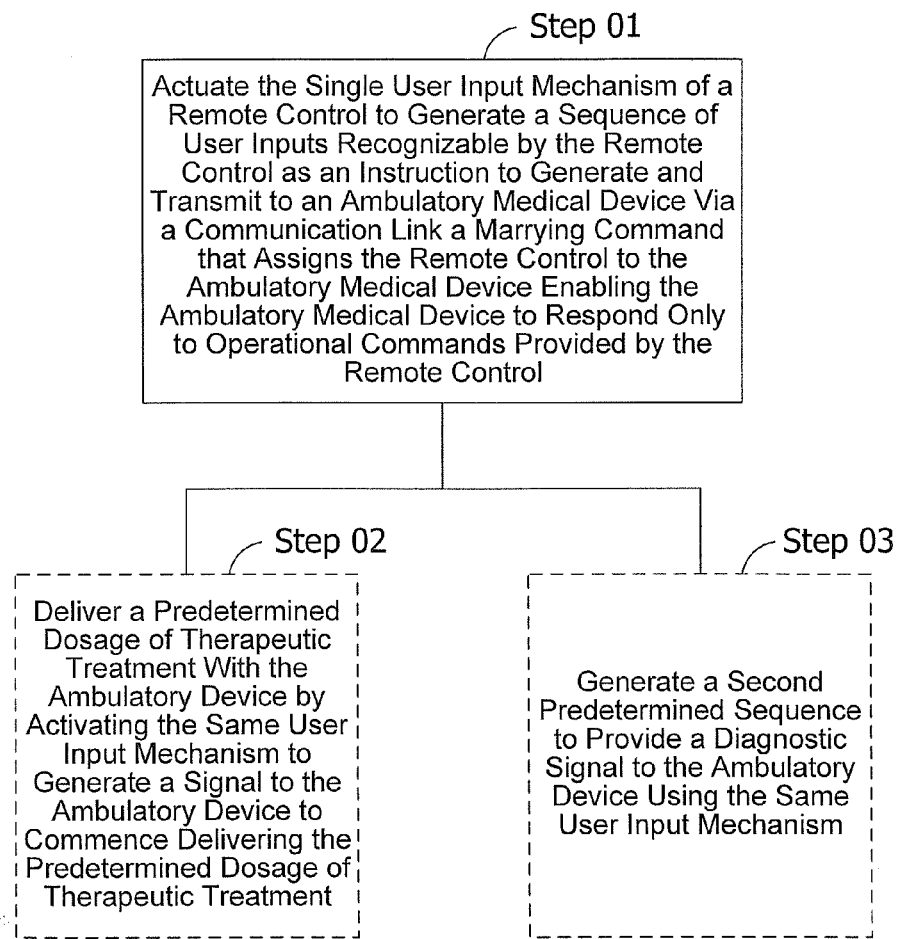
FIG. 7 is a flow chart in accordance with one embodiment of a present invention.

FIG. 7 is a flow chart in accordance with one embodiment of a present invention. Step 01 provides that the user (e.g., physician, health care professional, patient, etc.): actuate the single user input mechanism of a remote control to generate a sequence of user inputs recognizable by the remote control as an instruction to generate and transmit to an ambulatory medical device via a communication link a marrying command that assigns the remote control to the ambulatory medical device enabling the ambulatory medical device to respond only to operational commands provided by the remote control. In this example embodiment, the term "operational commands" includes both bolus delivery signals as well as diagnostic signals. Thus, once the remote control is operationally associated with the ambulatory medical device by successfully executing Step 01, either Step 02 (deliver a predetermined dosage of therapeutic treatment with the ambulatory device by activating the same user input mechanism to generate a signal to the ambulatory device to commence delivering the predetermined dosage of therapeutic treatment) or Step 03 (generate a second predetermined sequence to provide a diagnostic signal to the ambulatory device using the same user input mechanism) can then be taken using the remote control.

In an example embodiment, a method of communicating between a remote control device and an ambulatory device includes marrying a remote control device with an ambulatory device by providing a predetermined sequence of user inputs using a user input mechanism on the remote control device, and after the marrying step is completed, delivering a predetermined dosage of therapeutic treatment with the ambulatory device by activating the same user input mechanism to generate a signal to the ambulatory device to commence delivering the predetermined dosage of therapeutic treatment.

In an example embodiment, a method of operating a remote control device and ambulatory device includes generating a first predetermined sequence to marry a remote control device with an ambulatory device by providing a predetermined sequence of user inputs using a user input mechanism on the remote control device, and generating a second predetermined sequence to provide a diagnostic signal to the ambulatory device using the same user input mechanism. In an example embodiment, the method further includes uplinking the diagnostic signal to generate a status indicator concerning diagnostics.

In an example embodiment, a method for assigning a remote control to an ambulatory medical device includes generating and transmitting user inputs from a remote control to an ambulatory medical device, and receiving and processing the user inputs to determine whether the user inputs represent a sequence authorizing an assignment of the remote control to the ambulatory medical device. By way of example, the sequence specifies a predetermined number of user inputs, or a predetermined number and pattern of user inputs. The predetermined number of user inputs can be two, three, four, or any other number.

In an example embodiment, the method further includes providing a user prompt for an additional user input (e.g., an assignment confirmation input). For example, the user prompt is generated after the sequence authorizing an assignment has been provided. In an example embodiment, the user prompt is generated after a signal generated by the ambulatory medical device is received by the remote control.

The user prompt can be generated by any of the status indicators on either the remote control device or the ambulatory medical device. For example, the user prompt is generated by controlling one or more light sources to flash at the remote control. In an example embodiment, the user prompt is one or more of an audible sound in the remote control, an audible sound in the ambulatory medical device, a visual indication on the remote control, and a vibration of the remote control. In another example embodiment, the remote control has a sound source for producing at least two distinguishable sounds.

In various embodiments, the sequence specifies a temporal requirement for providing one or more of the user inputs. For example, the temporal requirement is a maximum amount of time that the user input mechanism can be actuated in order to provide one or more of the user inputs. Also by way of example, the temporal requirement is a minimum amount of time that the user input mechanism can be actuated in order to provide one or more of the user inputs. Additionally, the temporal requirement can be a maximum time interval allowed between two of the user inputs. In an example embodiment, the temporal requirement includes a maximum amount of time the user input mechanism can be activated in order to provide one or more user inputs, a minimum amount of time that the user input mechanism can be activated in order to provide one or more user inputs, and a maximum time interval allowed between two of the user inputs.

Figure 8:
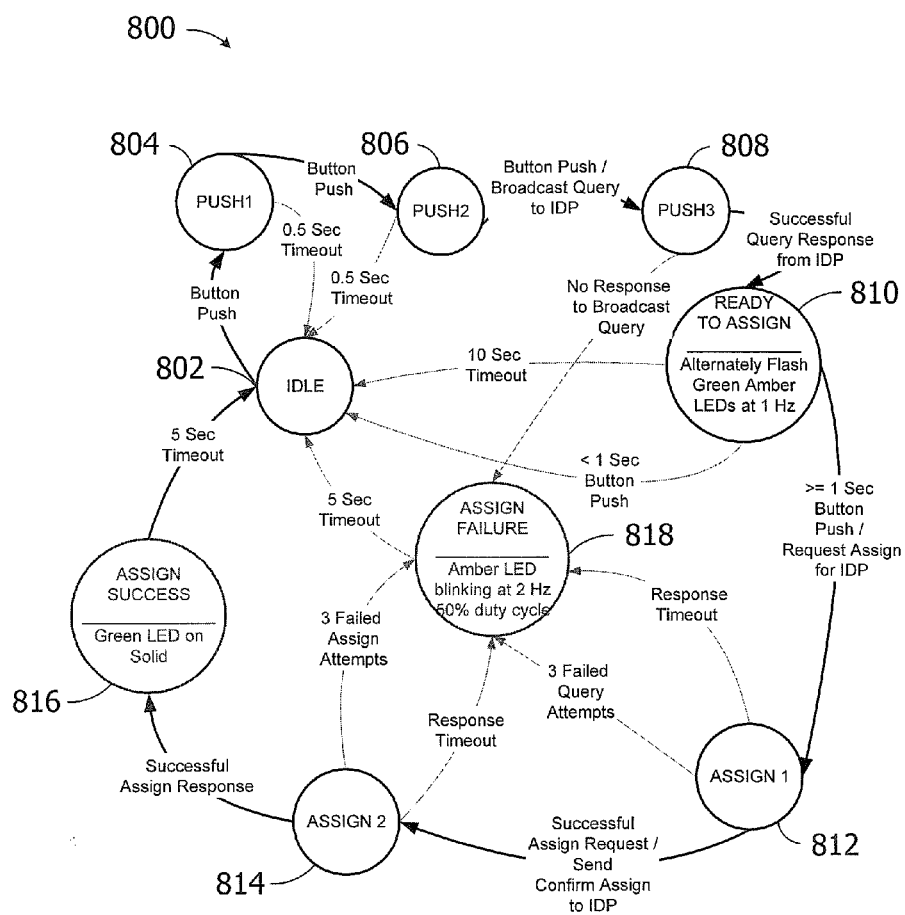
FIG. 8 is a state machine in accordance with one embodiment of a present invention.

FIG. 8 is a state machine 800 in accordance with one embodiment of a present invention. In this example embodiment, three rapid user inputs (e.g., button presses) provided in succession put the patient remote (PR) in the "ready to assign" state 810 for up to ten seconds. In an example embodiment, the state machine 800 specifies a maximum amount of time (e.g., 0.2 seconds) the user input mechanism can be activated in order to provide each of the user inputs at states 804, 806, and 808, as well as a maximum time interval allowed (e.g., 0.5 seconds) between the user inputs provided at states 804, 806, and 808. It should be appreciated that these temporal requirements can be varied, and that the number and/or pattern of user inputs can also be varied. At state 810, two LEDs (e.g., green and amber) are controlled to alternately flash at 1 Hz. This provides an indication of the "ready to assign" state to the user. As discussed above, an audio speaker and/or vibration device can instead (or additionally) be used to provide status indications, user prompts, and the like.

In this example embodiment, the user is prompted (as described above) during the "ready to assign" state 810 to provide an additional user input. More specifically, in this example embodiment, the user has 10 seconds to continuously press the button for at least one second, which generates a query for the Implantable Drug Pump (IDP). If the user "times out" by failing to provide the additional input within 10 seconds, or if the user does not continuously provide the additional input for at least one second, he or she is returned to the Idle state 802. At Assign 1 state 812, up to three Query Attempts are made (e.g., with a 2 second timeout specified). If there is a successful Query Response, the state machine 800 advances to the Assign 2 state 814 where assignment of the PR to the IDP is attempted. At Assign 2 state 814, up to three Assign Attempts are made (e.g., with a 2 second timeout specified). If there is a successful Assign Response, the state machine 800 advances to the Assign Success state 816, and the green LED is illuminated solid (FIG. 9A). However, if there are three failed Query Attempts or Assign Attempts, the state machine 800 advances to the Assign Failure state 818, and the amber LED is illuminated at 2 Hz 50% duty cycle (FIG. 9B).

FIG. 10 is a display lights legend for a remote control device in accordance with one embodiment of the present invention. This legend demonstrates that the status indicators can be controlled for multiple purposes including, but not limited to, providing indications relating to "marrying" (or attempting to "marry") a remote control device to an ambulatory device, bolus requests, available battery power. In this example embodiment, a Ready to Assign status is indicated by alternately illuminating amber and green LEDs. It should be understood that LEDs or light sources of any color or combination of colors can be used, and that the display light patterns can be varied. For example, it may be appropriate to use a greater variety of patterns when only a single LED or other light source is included in the remote control device. A remote control device with a single LED, single color of LED, or alarm (audible speaker or vibration device) adapted to provide user prompts and status indicators may be particularly beneficial for the visually impaired or color blind. For example, the controller 138 is instead adapted to control the alarm 147 (e.g., an audio speaker) to generate sequences of tones which represent a status and/or user prompt. Alternately, the controller can include voice synthesizer functionality and be adapted to control the audio speaker to generate more human friendly indications (i.e., audible voice reading words or phrases, such as "Ready to Assign", etc.)

Referring to FIGS. 11-15, the exemplary remote control 100 includes a housing 102 and a button 104. The housing 102 carries a movable button control element 106 with a depressible member 108 that is positioned over the button 104. As discussed in greater detail below, the remote control 100 will generate a signal when the button 104 is pressed and, depending on its position, the button control element 106 will control the operation of the button by either preventing or allowing the button to be pressed.

Figure 11:
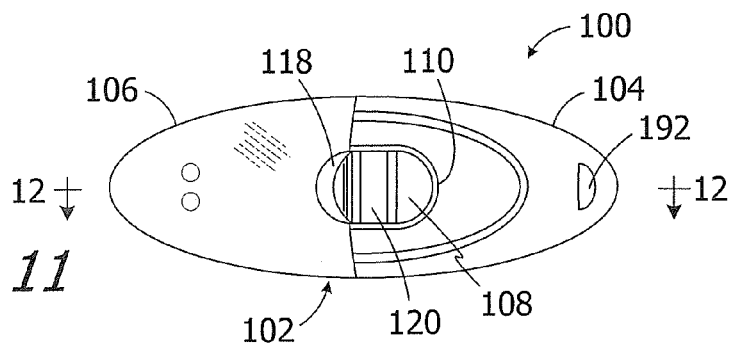
FIG. 11 is a plan view of a remote control in a locked state in accordance with one embodiment of a present invention.
Figure 12:
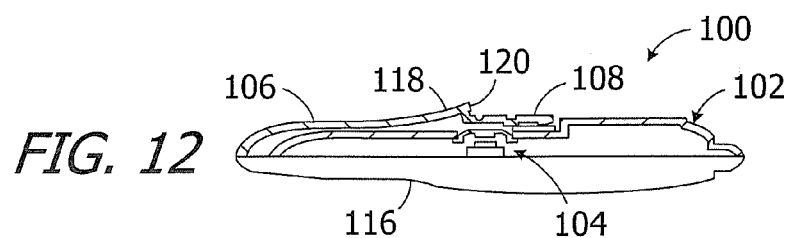
FIG. 12 is partial section view taken along line 12-12 in FIG. 11.

The exemplary remote control 100 is shown in the locked state, i.e. the state in which the button 104 may not be pressed, in FIGS. 11 and 12. More specifically, when the movable button control element 106 is in the position illustrated in FIGS. 11 and 12, the depressible member 108 will be aligned with a barrier 110 (FIG. 13) on the housing 102. The barrier 110, which may include abutments 112, prevents the depressible member 108 on the button control element 106 from being depressed, thereby preventing the button 104 from being pressed.

Figure 13:
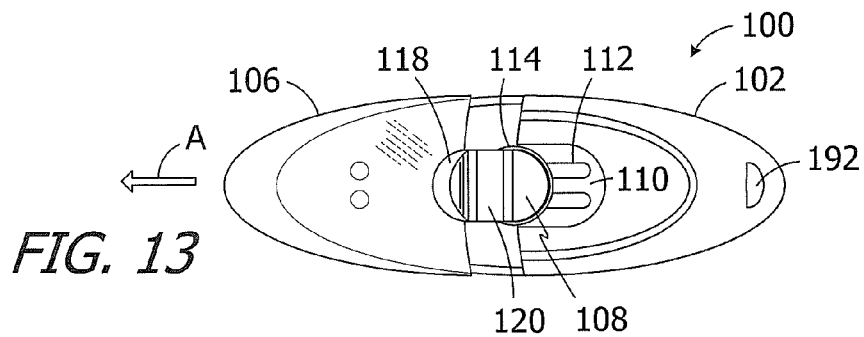
FIG. 13 is a plan view of the remote control illustrated in FIG. 11 in an unlocked state.
Figure 14:
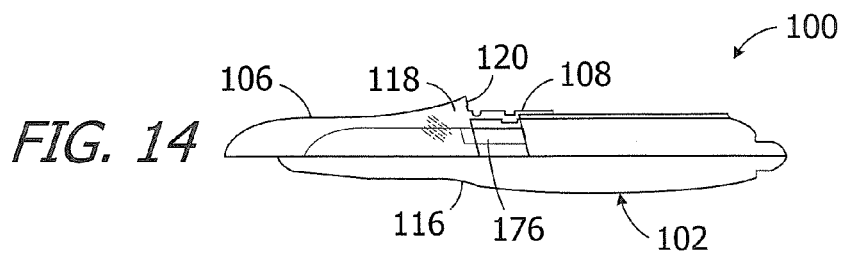
FIG. 14 is a side view of the remote control illustrated in FIG. 11 in an unlocked state.

The exemplary remote control 100 may be adjusted to the unlocked state illustrated in FIGS. 13 and 14, i.e. the state in which the button 104 may be pressed, by moving the button control element 106 in the direction of arrow A until the depressible member 108 is no longer aligned with the barrier 110 and is instead aligned with a housing aperture 114 that is adjacent to the barrier. To that end, the housing 102 in the exemplary embodiment includes a surface 116 that is shaped to receive the user's forefinger and the button control element 106 includes a raised area 118 that combines with the depressible member 108 to form a region that is shaped to receive the user's thumb. This configuration allows the user to easily hold the remote control 100 between his or her thumb and forefinger and slide the button control element 106 with the thumb. The depressible member 108 and raised area 118 also include ridges 120 which prevent the user's thumb from slipping. Once the button control element 106 has reached the unlocked position illustrated in FIGS. 13 and 14, the user will be able to press the button 104 by moving the depressible member 108 in the direction indicated by arrow B in FIG. 15. This may be easily accomplished by simply pressing downwardly with the thumb.

The housing 102 and button control element 106 perform the advantageous function of preventing inadvertent communication between the exemplary remote control 100 and the associated medical device by preventing the button 104 from being pressed unless the user has demonstrated his/her intent to press the button. Such intent is demonstrated, in the context of the exemplary remote control 100, by sliding the button control element 106 from the locked position (FIGS. 11 and 12) to the unlocked position (FIGS. 13 and 14) prior to pressing the button 104.

Figure 15:
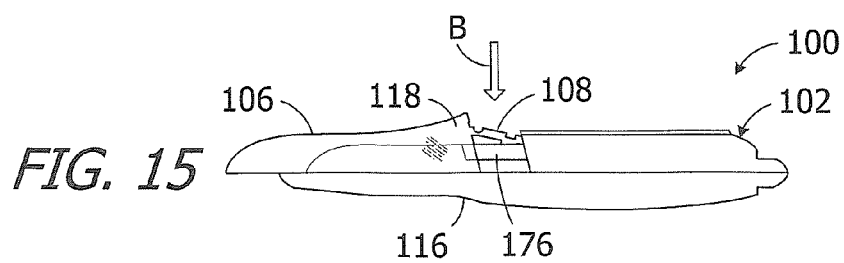
FIG. 15 is a side view of the remote control illustrated in FIG. 11 in an unlocked state and actuated state.

There are a variety of structural configurations that would allow a remote control to move from a locked state to an unlocked state in the manner illustrated in FIGS. 11-14, and then be actuated in the manner illustrated in FIG. 15. One example of such a configuration is described below with reference to FIGS. 16-23.

Referring first to FIGS. 16-19, the exemplary housing 102 includes a bottom member 122 and a top member 124. The bottom member 122 has a main wall 126, an outer wall 128 that extends around the perimeter of the main wall, and inner walls 130 and 132. The inner walls 130 and 132 define storage regions for a circuit board 134 and a battery 136. The circuit board 134 carries a controller 138, a communication device 140 (including an antenna), an actuator 142 with a movable element 144, and a pair of LEDs 146 (or other light emitting elements). The movable element 144 is aligned with the housing aperture 114 and, in the illustrated embodiment, the housing aperture is covered by a resilient cover 148 that keeps dirt and moisture out of the closed interior space within the housing 102. The actuator 142 may be, for example, a normally open switch that is biased to the open state and is closed in response to downward (in the illustrated orientation) movement of the movable element 144, as is discussed in greater detail below with reference to FIG. 23.

The exemplary button 104, which consists of the actuator 142 and the resilient cover 148, may be pressed by depressing the depressible member 108 when the remote control 100 is in the unlocked state (FIGS. 13-15). Specifically, the depressible member 108 will press the resilient cover 148 which, in turn, will press the movable element 144 of the actuator 142 and close the switch. In some alternative embodiments, the housing aperture 114 will be uncovered and the depressible member 108 will come into direct contact with the actuator 142. In either case, the controller 138 will instruct the communication device 140 to transmit a signal when the switch is closed.

Figure 16:
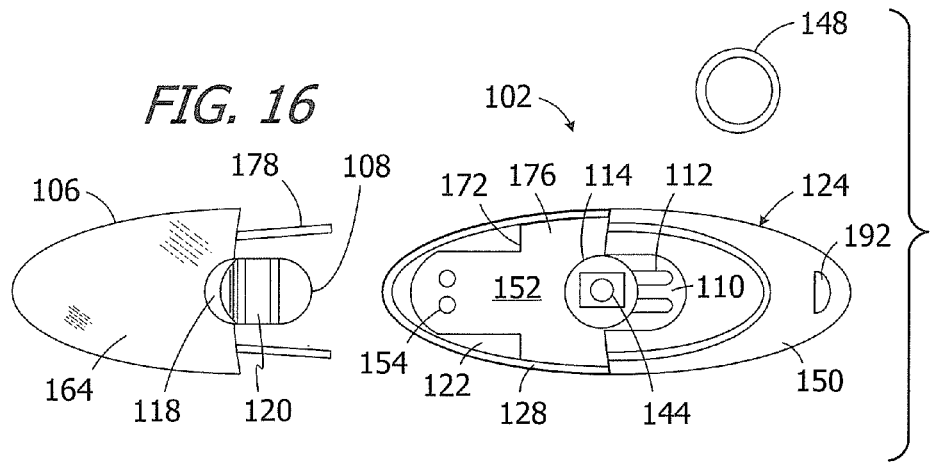
FIG. 16 is a partially exploded view of the remote control illustrated in FIG. 11.
Figure 17:
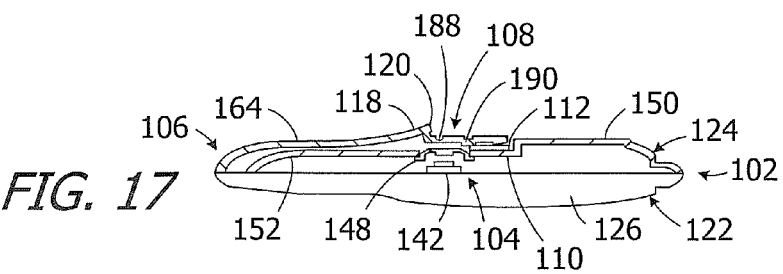
FIG. 17 is a side, partial section view of the remote control illustrated in FIG. 11 in a locked state.
Figure 18:
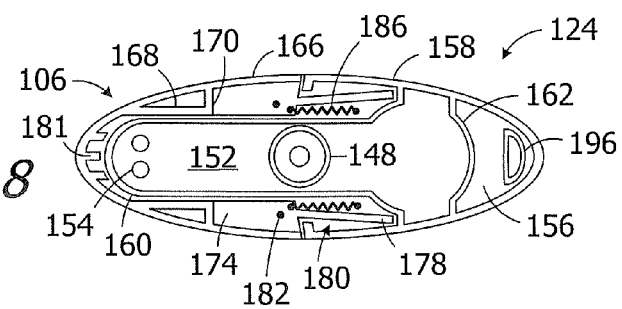
FIG. 18 is a plan view of the underside of an exemplary housing top member in a locked state.
Figure 19:
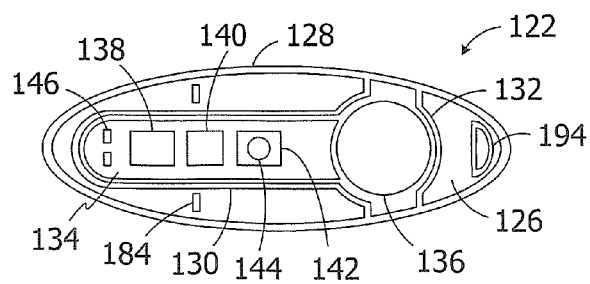
FIG. 19 is a plan view of an exemplary housing bottom member.
Figure 20:
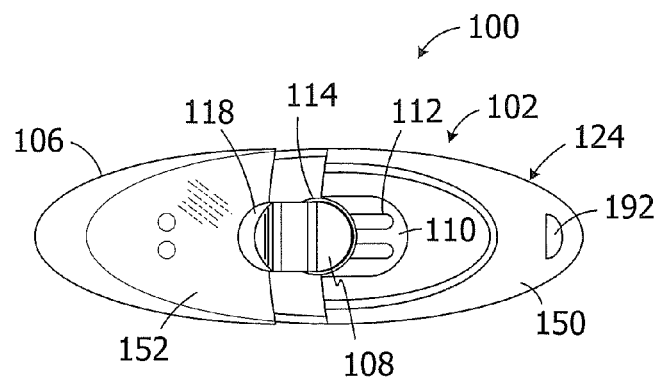
FIG. 20 is a plan view of the remote control illustrated in FIG. 11 in an unlocked state.
Figure 21:
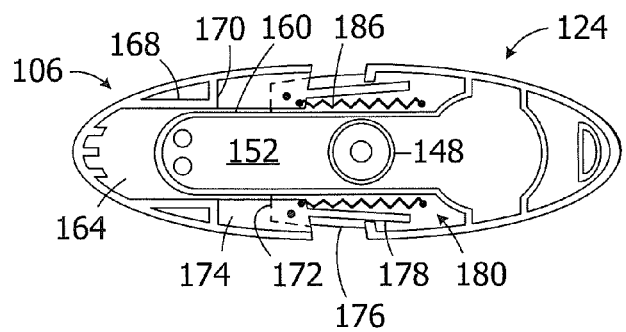
FIG. 21 is a plan view of the underside of the housing top member illustrated in FIG. 18 in an unlocked state.
Figure 22:
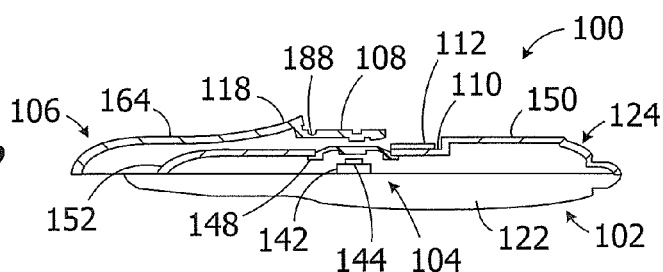
FIG. 22 is a side, partial section view of the remote control illustrated in FIG. 11 in an unlocked state.

As illustrated in FIGS. 16-18, the top member 124 of the exemplary housing 102 covers the bottom member 122, thereby defining a closed interior space, and also includes the housing aperture 114. The top member 124 may, for purposes of this description, be divided into a first section 150 that is generally aligned with the button control element 106, and a second section 152 that is located below the button control element. The barrier 110 and housing aperture 114 are part of the second section 152 and the barrier is located between the housing aperture and the first section 150. The second section 152 includes light apertures 154 that allow light from the LEDs 146 to pass through the housing 102. To that end, it should also be noted here that the button control element 106 in the illustrated embodiment is translucent. As such, light from the LEDs 146 that passes through the light apertures 154 will be visible to the user.

With respect to its other structural elements, the top member 124 illustrated in FIGS. 16-18 has a main wall 156 that forms the first and second sections 150 and 152, an outer wall 158, and inner walls 160 and 162. The outer and inner walls 128-132 of the bottom member 122 abut the outer and inner walls 158-162 of the top member 124. The bottom member 122 may also be provided with a plurality of holes (not shown), and the top member 124 may also be provided with a corresponding plurality of posts (not shown) that are configured to be interference fit into the holes to secure the top member to the bottom member.

Turning to the exemplary movable button control element 106, and referring to FIGS. 16-18, the button control element includes a main wall 164 and an outer wall 166. The button control element 106 is also configured to slide along the second section 152 of the housing top member 124. To that end, the button control element 106 is provided with a pair of longitudinally extending inner walls 168 that are in close proximity to, as well as parallel to, the two longitudinally extending portions of the top member inner wall 160. The button control element 106 also has transversely extending inner walls 170 that are positioned such that they abut transversely ending walls 172 (FIGS. 14-16) on the top member 124, thereby limiting the range of movement of the button control element relative to the housing 102. The button control element 106 also includes covers 174 (FIG. 18) that extend inwardly from the outer wall 166. The wide portions 176 (FIG. 16) of the top member second section 152 slide within the spaces defined by the covers 174 and the button control element main and outer walls 164 and 166. The button control element 106 is provided with a pair of guides 178 which slide within a corresponding pair of slots 180 (FIG. 18) that are located within the first section 150 of the housing top member 124. Finally, the button control element 106 includes a plurality of stop members 181 that engage the curved portion of the inner wall 160 on the housing top member 124.

The longitudinally extending portions of the top member inner wall 160, the movable portion inner walls 168, the covers 174, the top member wide portions 176, the guides 178 and slots 180 individually and collectively prevent the movable button control element 106 from sliding in any direction other than along the longitudinal axis of the housing 102. The orientation of the longitudinal axis is the same as the orientation of arrow A in FIG. 13. As a result, even in those instances where the user applies a pushing force to the button control element 106 which has a component that is transverse to longitudinal axis, the button control element will move in the longitudinal direction indicated by arrow A. The guides 178 also prevent debris from entering the housing 102 when the button control element 106 is in the unlocked position.

The covers 174 and the top member wide portion 176 also prevent the button control element 106 from being moved upwardly (in the orientation illustrated in FIG. 17) and pulled off the housing top member 124. Similarly, the alignment of the housing first section 150 with the button control element 106 (including the depressible member 108) prevents a fingernail or object from getting under, and lifting, the depressible member when the remote control 100 is in the locked state.

Forward movement of the button control element 106 relative to the housing 102, i.e. movement toward the unlocked position, is limited by a pair of pins 182 (FIG. 18) that extend downwardly from the covers 174 and engage a pair of stop members 184 (FIG. 19) on the housing bottom member 122 when the button control element reaches the unlocked position illustrated in FIG. 13. Rearward movement is limited by the transversely extending walls 170 and 172, as well as the stop members 181 and the curved portion of the inner wall 160.

The button control element 106 is biased to the locked position illustrated in FIGS. 11, 12, 17 and 18. Thus, unless the user is applying force to button control element 106 in the direction of arrow A (FIG. 13), the button control element will remain in the locked position and the depressible member 108 will remain on the barrier 110. Although the present inventions are not limited to any particular biasing arrangement, the exemplary remote control 100 includes a pair of tension springs 186. The tension springs 186 may be attached to the button control element 106 and to the housing top member 124. The tension springs 186 also help prevent the button control element 106 from being pulled off of the housing 102.

As noted above, the depressible member 108 is part of the button control element 106 and rests on the barrier abutments 112 when the exemplary remote control 100 is in the locked state. More specifically, in the illustrated embodiment, the depressible member 108 is secured to the remainder of the button control element 106 by a living hinge 188 (FIG. 17) and includes a pair of downwardly extending protrusions 190 that rest on the barrier abutments 112. The living hinge 188 allows the depressible member 108 to pivot from the position illustrated in FIG. 14 to the position illustrated in FIG. 15. The living hinge 188 also biases the depressible member 108 to the position illustrated in FIG. 14. The living hinge bias provides an additional level of safety in that simply overcoming the biasing force on the button control element 106 and moving the button control element to the unlocked position will not, in and of itself, result in the button 104 being pressed and a signal being generated. The user must also press the depressible member 108 while maintaining the button control element 106 in the unlocked position.

The manner in which some of the structural elements described above with reference to FIGS. 16-19 operate, as the exemplary remote control 100 is moved from the locked state to the unlocked state, are described below with reference to FIGS. 20-23. With respect to the interaction between the housing 102 and the button control element 106, the longitudinally extending inner walls 168 on the button control element slide along the longitudinally extending portions of the housing inner wall 160, and the transversely extending inner walls 170 on the button control element pull away from the transversely ending walls 172 on the housing. The spaces defined by the button control element main wall 164 and covers 174 will no longer completely enclose the wide portions 176 of the housing second section 152, and the button control element guides 178 will no longer be completely within the housing slots 180. The springs 186, which bias the button control element 106 to the locked position, will also stretch.

Figure 23:
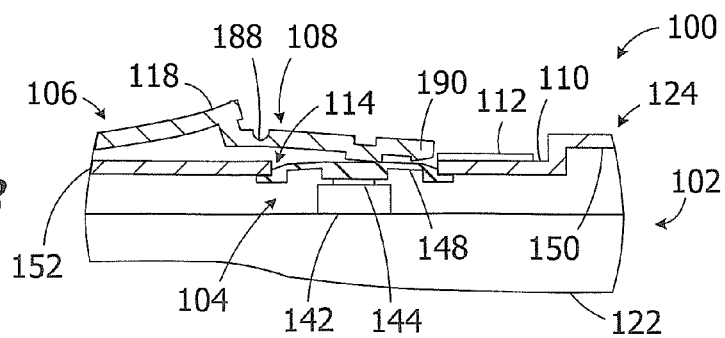
FIG. 23 is a side, partial section view of a portion the remote control illustrated in FIG. 11 in an unlocked and actuated state.

The exemplary remote control 100 is shown in the unlocked and actuated state (i.e. with the button 104 pressed) in FIG. 23. The depressible member 108 is aligned with the aperture 114 and pivoted about the living hinge 188 into contact with the resilient cover 148. As a result of the downward force applied by the depressible member 108, the resilient cover 148 is collapses and presses the movable element 144 on the actuator 142, thereby causing the remote control 100 to generate a signal.

The exemplary housing 102 is also provided with an opening 192 that allows the remote control 100 to be secured to, for example, a band of material and worn like a necklace or to a connector ring that facilitates connection to a key chain or a belt loop. The housing top and bottom members 122 and 124 may respectively include sealing walls 194 and 196 (FIGS. 18 and 19) that contact one and other and prevent dirt and moisture from entering the housing 102 by way of the opening 192.

Although the present inventions are not limited to any particular sizes, the exemplary remote control 100 may be sized such that it can be conveniently held between the thumb and forefinger and/or placed in the user's pocket. In one exemplary implementation, the remote control 100 is about 7.5 cm long, 3.5 cm wide and, at its thickest region, about 1.5 cm thick.

Although the inventions disclosed herein have been described in terms of the preferred embodiments above, numerous modifications and/or additions to the above-described preferred embodiments would be readily apparent to one skilled in the art. The inventions also include any combination of the elements from the various species and embodiments disclosed in the specification that are not already described. It is intended that the scope of the present inventions extend to all such modifications and/or additions and that the scope of the present inventions is limited solely by the claims set forth below. Additionally, the present inventions include systems that comprise an ambulatory medical device (such as an implantable infusion device) in combination with any of the remote controls described above or claimed below.

What is claimed is:

1. A remote control apparatus for use with an ambulatory medical device, the remote control apparatus comprising:
    a user input mechanism adapted to be actuated to generate user inputs;
    a communication device adapted to facilitate a communication link between the remote control apparatus and the ambulatory medical device; and
    a controller adapted to control the communication device in response to the user input mechanism being actuated, and to receive and process the user inputs to determine whether the user inputs represent a sequence that specifies a predetermined number of the user inputs, said predetermined number being two or more, authorizing an assignment of the remote control apparatus to the ambulatory medical device;
    wherein the remote control apparatus has only a single user operated control, which user operated control is the user input mechanism.

2. The remote control apparatus of claim 1, wherein the single user operated control is a pressable button.

3. The remote control apparatus of claim 1, wherein the controller is adapted to generate and control the communications device to transmit a command to the ambulatory medical device to generate an audible sound after the sequence has been provided.

4. The remote control apparatus of claim 1, further comprising:
    one or more light sources;
    wherein the controller is adapted to control the one or more light sources to provide a user prompt for an additional user input.

5. The remote control apparatus of claim 4, wherein the one or more light sources is two light sources.

6. The remote control apparatus of claim 1, further comprising:
    a memory device;
    wherein the controller is adapted to store in the memory device ambulatory medical device identification information transmitted from the ambulatory medical device to the remote control apparatus via the communication link.

7. The remote control apparatus of claim 6, wherein the controller is adapted to store the ambulatory medical device identification information in the memory device after an assignment confirmation input has been provided via the user input mechanism.

8. The remote control apparatus of claim 6, wherein the controller is adapted to control the communications device to transmit remote control identification information after an assignment confirmation input has been provided via the user input mechanism.

9. The remote control apparatus of claim 1, wherein the ambulatory medical device is an infusion pump.

10. The medical device system of claim 1, wherein the controller is adapted, in relation to a process of assigning the remote control apparatus to the ambulatory medical device, to utilize the user input mechanism in a manner distinguishable from other operations effected utilizing the user input mechanism, said other operations including one or more of commanding a bolus and sending a diagnostic signal.

11. The remote control apparatus of claim 1, wherein the controller is adapted to allow, after the remote control apparatus is assigned to the ambulatory medical device, the delivery of a predetermined dosage of therapeutic treatment with the ambulatory medical device by activating the user input mechanism to generate a signal to the ambulatory medical device to commence delivering the predetermined dosage of therapeutic treatment.

12. A medical device system comprising:
- a remote, the remote having only a single user operated control, which is a single user input mechanism adapted to be actuated by a user of the remote to generate a user input;
- an implantable drug pump; and
- a communication link between the remote and the implantable drug pump;
- wherein the remote includes a controller adapted to control the communication link in response to the single user operated control being actuated, and to receive and process user inputs generated by the single user operated control to determine whether the user inputs represent a sequence of two or more of the user inputs recognizable by the controller as an instruction to generate and transmit to the implantable drug pump via the communication link a marrying command that assigns the remote to the implantable drug pump enabling the implantable drug pump to respond only to operational commands provided by the remote;
- wherein the controller is adapted, in relation to a process of assigning the remote to the implantable drug pump, to utilize the user input mechanism in a manner distinguishable from other operations effected utilizing the user input mechanism, said other operations including one or more of commanding a bolus and sending a diagnostic signal.

13. The medical device system of claim 12 wherein the sequence specifies that the predetermined number of user inputs are provided to the remote prior to generation of a user prompt for an additional user input, said additional user input being an assignment confirmation input.

14. The medical device system of claim 12, wherein the controller is adapted to allow, after the remote is assigned to the implantable drug pump, the delivery of a predetermined dosage of therapeutic treatment with the implantable drug pump by activating the single user input mechanism to generate a signal to the implantable drug pump to commence delivering the predetermined dosage of therapeutic treatment.

15. A method for communicating between a remote control and an implantable drug pump, the remote control having only a single user operated control, which single operated control is a user input mechanism adapted to be actuated by a user of the remote control to generate a user input, the remote control being adapted to facilitate a communication link with the implantable drug pump, the method including:
- actuating the single user input mechanism of the remote control to generate a sequence of user inputs recognizable by the remote control as an instruction to generate and transmit to the implantable drug pump via the communication link a marrying command that assigns the remote control to the implantable drug pump enabling the implantable drug pump to respond only to operational commands provided by the remote control; and
- after the marrying command assigns the remote control to the implantable drug pump, allowing the delivery of a predetermined dosage of therapeutic treatment with the implantable drug pump by activating the single user input mechanism to generate a signal to the implantable drug pump to commence delivering the predetermined dosage of therapeutic treatment.

16. The method of claim 15, wherein the sequence of user inputs recognized by the remote control is provided uninterrupted by a prompt for an additional user input.

17. The method of claim 15, further comprising:
- signaling to the user through user prompts generated by a status indicator when the sequence of user inputs has been received.

18. The method of claim 15, wherein the sequence is a predetermined number and pattern of user inputs.

19. The method of claim 15, wherein the sequence specifies a temporal requirement for providing one or more of the user inputs.

20. The method of claim 15, further comprising:
- in relation to a process of assigning the remote control to the ambulatory medical device, the remote control utilizing the user input mechanism in a manner distinguishable from other operations effected utilizing the user input mechanism, said other operations including one or more of commanding a bolus and sending a diagnostic signal.

* * * * *